(12) United States Patent
Dubey et al.

(10) Patent No.: US 9,642,886 B2
(45) Date of Patent: May 9, 2017

(54) PLANT BASED FORMULATION FOR THE PREVENTION AND MANAGEMENT OF METABOLIC SYNDROME BY ITS ADIPONECTIN ENHANCING PROPERTY

(71) Applicant: SRM UNIVERSITY, Kattankulathur (IN)

(72) Inventors: Govind P. Dubey, Kattankulathur (IN); Murugesan Ponnavaikko, Kattankulathur (IN); Aruna Agarwal, Varansi (IN); Nirupama Dubey, Kattankulathur (IN); Shipra Dubey, Kattankulathur (IN)

(73) Assignee: SRM UNIVERSITY, Kattankulathur (IN)

( * ) Notice: Subject to any disclaimer, the term of this patent is extended or adjusted under 35 U.S.C. 154(b) by 0 days.

(21) Appl. No.: 14/468,285

(22) Filed: Aug. 25, 2014

(65) Prior Publication Data

US 2016/0051617 A1 Feb. 25, 2016

(51) Int. Cl.
| | | |
|---|---|---|
| *A61K 36/9066* | (2006.01) | |
| *A61K 36/37* | (2006.01) | |
| *A61K 36/185* | (2006.01) | |
| *A61K 36/8945* | (2006.01) | |

(52) U.S. Cl.
CPC ........ *A61K 36/9066* (2013.01); *A61K 36/185* (2013.01); *A61K 36/37* (2013.01); *A61K 36/8945* (2013.01)

(58) Field of Classification Search
None
See application file for complete search history.

(56) References Cited

U.S. PATENT DOCUMENTS 6,376,682 B1 * 4/2002 Yamahara ............ C07D 333/46
549/62

FOREIGN PATENT DOCUMENTS

| EP | 2 042 183 A1 * | 4/2009 |
| IN | 200901996 I1 * | 10/2011 |
| JP | 2010202634 A * | 9/2010 |

OTHER PUBLICATIONS

"How Do You Treat Metabolic Syndrome" website (https://web.archive.org/web/20071107204753/http://www.webmd.com/heart/metabolic-syndrome/how-do-you-treat-metabolic-syndrome—Internet archived version from Nov. 7, 2007).*
Phillips (Journal of Ethnopharmacology (2006), vol. 104, pp. 351-355).*

* cited by examiner

*Primary Examiner* — Susan Hoffman
(74) *Attorney, Agent, or Firm* — Venable LLP; Keith G. Haddaway

(57) ABSTRACT

The invention relates to a plant based formulation for the prevention and management of metabolic syndrome by its adiponectin enhancing property comprising of an effective amount of hydro-methanolic extract of *Salacia reticulata*, *Tribulus terrestris*, *Curcuma longa* and *Dioscorea bulbifera* and optionally additives in trace amounts.

9 Claims, 11 Drawing Sheets

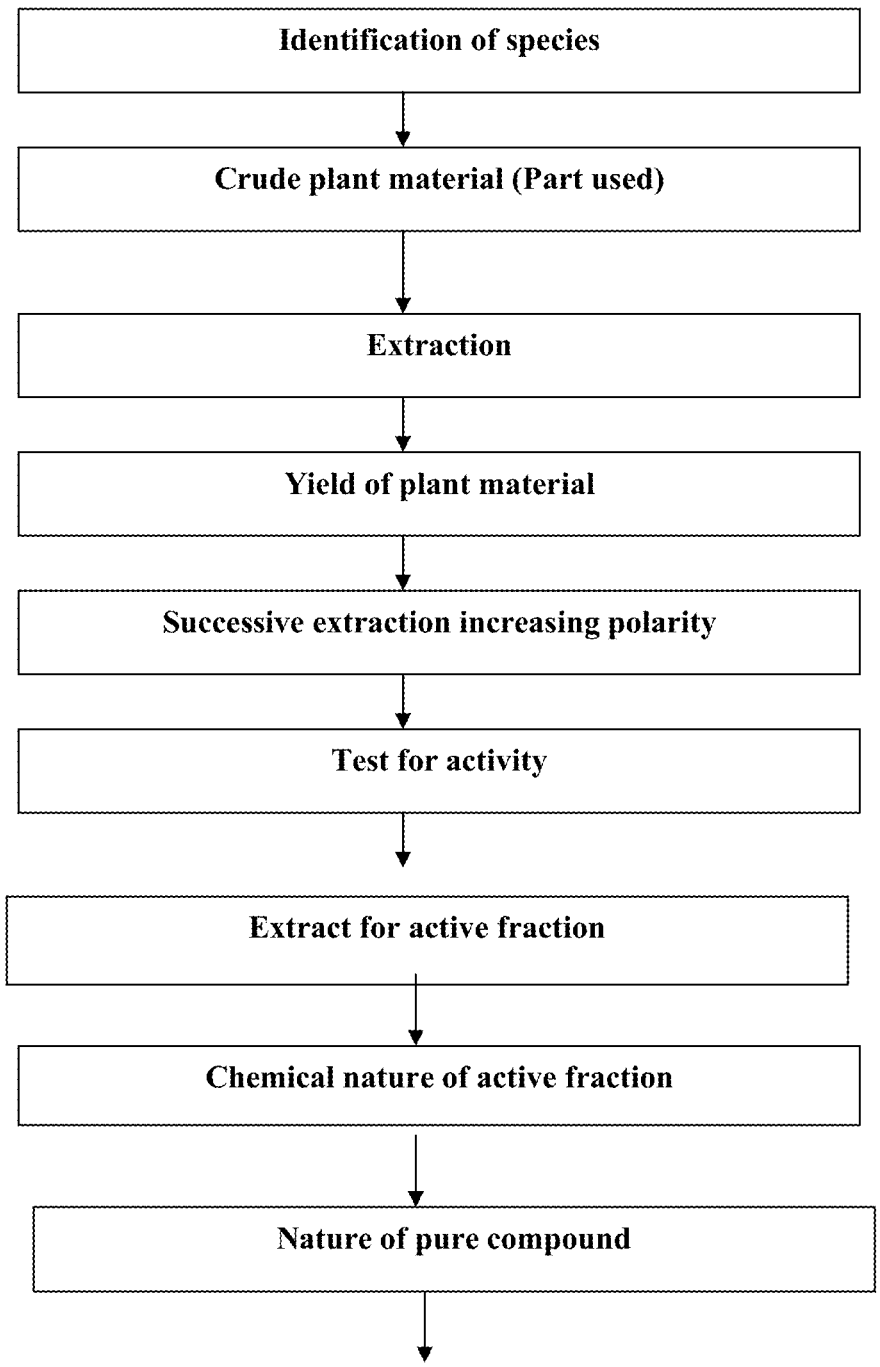

PLANT BASED FORMULATION FOR THE PREVENTION AND MANAGEMENT OF METABOLIC SYNDROME BY ITS ADIPONECTIN ENHANCING PROPERTY

FIELD OF INVENTION

The present invention relates to a herbal based formulation for the prevention and management of metabolic syndrome by its adiponectin enhancing property. The formulation of present invention may be advantageous if used for the prevention and management of insulin resistance, dyslipidemia including atherosclerosis and vascular inflammation in metabolic syndrome patients particularly its beneficial effect on adiponectin, leptin, resistin, serum insulin, glycosylated hemoglobin, oxidized LDL-c, triglycerides, interleukin-6, TNF-α including hs CRP.

BACKGROUND OF INVENTION

The metabolic syndrome represents a combined occurrence of atherogenic dyslipidemia, insulin resistance, hypertension and obesity. It is established that obesity and metabolic syndrome significantly influence the onset of cardiovascular disorders particularly in presence of type-2 diabetes mellitus. Increasing incidence of obesity has markedly enhanced the prevalence of metabolic syndrome world wide. Pro-inflammatory and pro-thrombotic state, responsible for endothelial dysfunction is a common feature among metabolic syndrome cases. In metabolic syndrome the status of impaired glucose tolerance, insulin resistance, dyslipidemia and hypertension exhibits a pro-thrombotic state.

It is reported that about one quarter of adults and about nine percent of teenagers are having metabolic syndrome. Persons with metabolic syndrome are two times more at risk of developing heart disease and five times at risk of developing diabetes. The etiopathogenesis of metabolic syndrome is both genetic and environmental factors. Excess abdominal fat, defect in insulin action and energy storage are the major risk factors playing role in the occurrence of metabolic syndrome. According to the National Cholesterol Education Program of Adult Treatment Panel III (ATP-III) guidelines for identifying metabolic syndrome, the diagnosis is based upon the involvement of three or more of the components together like abdominal obesity, triglycerides, HDL-c, blood pressure and fasting glucose level.

Obesity play a major role in the development of metabolic syndrome. Obesity results from an imbalance between energy intake and energy expenditure. Both genetic as well as environmental factors are the predisposing factor for weight grain and causing obesity. Obesity management requires a drastic pharmacotherapy due to unsatisfactory results of diet control and exercise. Recently the anti-obesity agent sibutramine an appetite suppressant and Orlistat an inhibitor of fat absorption, is being used for the treatment of metabolic syndrome.

Maximum attention has been focused on the identification and treatment of dyslipidemia associated with metabolic syndrome. The abnormality in lipid metabolism with abdominal fat accumulation is well defined. An increased number of small dense LDL particles is constant feature of dyslipidemia of abdominal adiposity as they are associated with insulin resistance, intra-abdominal fat and hypertension. LDL comprises a spectrum of particles that vary in size, density, chemical composition and atherogenic potentials. The presence of small dense cholesterol-depleted LDL particles is associated with an increased risk of mycordial infarction and further worsens due to severity of cardiovascular disease. Due to the mechanism the small dense LDL particles enter in to the arterial wall more easily bind to arterial wall proteoglycans more avidly and are susceptible to oxidative modification, leading to macrophage uptake all of which may contributing to increased atherogenesis.

The evaluation of apolipo-B in the metabolic syndrome can help in targeting patients for aggressive lipid-lowering therapy. High levels of LDL-c are generally accepted to be one of the strongest risk factors for cardiovascular disease. Insulin resistance is associated with increased numbers of small VLDL-c and LDL-c particles, reflected by higher apolipo-B levels, with decreased triglyceride to apolipo-B ratios compared with those in individuals with normal insulin sensitivity. Studies have shown that increased apolipo-B and apolipo-B-containing lipoproteins (VLDL-c and LDL-c) are related to an increased risk of cardiovascular disease found significantly higher in individuals with metabolic syndrome.

Evidence suggests an association between chronic inflammation, insulin resistance, obesity, type-2 diabetes mellitus and arthrosclerosis. Recently, workers have reported that chronic inflammatory process may enhance insulin resistance and impaired β-cell function which are the risk factors for the occurrence of diabetes.

A number of studies have indicated that obesity and insulin resistance are associated with higher levels of markers of inflammation and endothelial function. Thus the relationship between various inflammatory markers particularly c-reactive protein and interleukin-6 and risk of development of type-2 diabetes mellitus is well established. Adiponectin i.e. adipocyte derived hormone has potentiality to down regulate inflammatory responses and also to improve glucose tolerance and insulin resistance. Adiponectin is related to insulin resistance and adiposity in humans and it is protective against the risk of development of diabetes.

Recently adiponectin has been discovered as a potential agent derived from adipose tissue. Low plasma levels of adiponectin are associated with insulin resistance, obesity, atherosclerosis, dyslipidemia and ultimately results in coronary heart disease. This hormones has been shown to be a key regulator of insulin sensitivity in human being. Adiponectin is an adipose tissues derived glycoprotein totally secreted by adipose tissue. Circulating adiponectin activates the peroxisome, proliferators activated receptor (PPAR-α) which are responsible for the regulation of glucose metabolism. Several workers have observed that hypo-adiponectenemia is a result of obesity indused, insulin resistance in adipose tissues. The molecular mechanism of insulin resistance specially in adipose tissues can only be understood from the study of endocrine regulation of energy metabolism and the role of various adipokines like leptin, ghrelin, adiponectin and resistin. All these above adipokines are produced by adipose tissues. The biological effects of adiponectin in humans have been a subjects of interests to the pharmacologist who are searching sub-specific targets who can regulates the abnormal anergy metabolism and can prevent the occurrence of insulin resistance, obesity and other related complications of metabolic syndrome. In case of insulin resistance plasma adiponectin is significantly less and this also associated with elevated levels of lipoprotein, glycemic index and dyslipidemia. It has been reported that adiponectin gene variants were one of the cause of obesity and insulin resistance.

Keeping the above facts in view it was proposed to develop a novel plant based formulation which has adiponectin enhancing property among metabolic syndrome patients so that atherosclerotic process and insulin resistance can be improved and future occurrence of adverse cardiac event may be prevented.

Scientific evaluation of some of the Ayurvedic drugs have shown better efficacy over standard pharmacologic therapies with minimum or without any side effect. The successful management of metabolic syndrome is seldom possible with a single drug entity as it is a disease condition clustering a group of abnormalities. In Ayurvedic system of medicine a comprehensive description as well as prevention and management strategies is given for obesity and diabetes. Thus taking lead from Ayurvedic classics the present test formulation has been prepared and evaluation on scientific parameters involved with metabolic syndrome particularly the adiponectin enhancing property of drugs is validated.

OBJECTS OF INVENTION

The primary object of present invention is to propose a plant based herbal formulation having adiponectin enhancing property so that patients of metabolic syndrome can be treated successfully without any adverse reaction.

Another object of present invention is to propose a plant based herbal formulation that can improve the insulin resistance among metabolic syndrome patients.

Yet another object of present invention is to propose a plant based Ayurvedic formulation beneficial in the prevention and management of abnormal lipids particularly oxidized LDL-c and triglycerides in metabolic syndrome patients.

Further, object of present invention is to propose a plant based Ayurvedic formulation having potential role in reducing elevated adipokines leptin and resist in involved with metabolic syndrome.

Still, another object of present invention is to propose a plant based herbal formulation showing adiponectin enhancing potential so that it can be effective in the management of vascular inflammation by reducing TNF-α, IL-6 and hs CRP in metabolic syndrome patients.

The foregoing has outlined some of the pertinent objectives of the invention. These objectives should not be construed to be merely illustrative of some of the more prominent features and applications of the intended invention. Many other beneficial results can be obtained by applying the disclosed invention in a different manner or modifying the invention within the scope of disclosure.

Accordingly, other objects and a full understanding of the invention and the detailed description of the preferred embodiment in addition to the scope of invention are to be defined by the claims herein.

These and other objects and advantages of the invention will be apparent from the ensuing description.

BRIEF DESCRIPTION OF DRAWINGS

Further objectives and advantages of this invention will be more apparent from the ensuing description when read in conjunction with the accompanying drawings wherein:

FIG. 1(a), FIG. 1(b) and

Figure 1B:
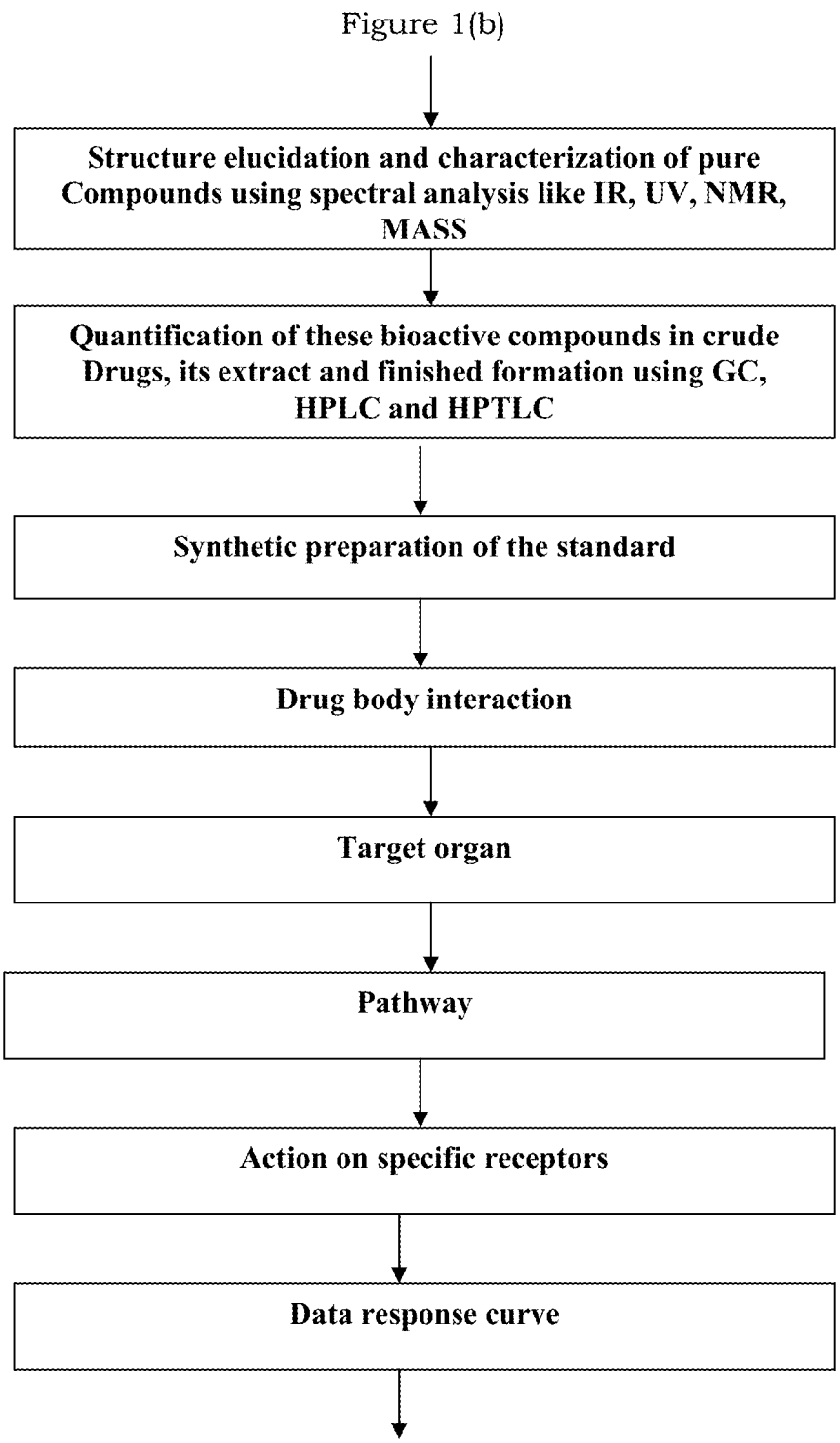

While the invention is described in conjunction with the illustrated embodiment, it is understood that it is not intended to limit the invention to such embodiment. On the contrary, it is intended to cover all alternatives, modifications and equivalents as may be included within the spirit and scope of the invention disclosure as defined by the claims.

STATEMENT OF INVENTION

According to this invention there is provided a plant based formulation for the prevention and management of metabolic syndrome by its adiponectin enhancing property comprising of an effective amount of hydro-methanolic extract of *Salacia reticulata, Tribulus terrestris, Curcuma longa* and *Dioscorea bulbifera* and optionally additives in trace amounts.

In other embodiments, the invention is a plant based formulation comprising *Dioscorea bulbifera* and at least two hydro-methanolic extracts selected from *Salacia reticulata, Tribulus terrestris*, and *Curcuma longa*. Exemplary formulations include hydro-methanolics extracts of *Salacia reticulata, Tribulus terrestris*, and *Dioscorea bulbifera*; hydro-methanolic extracts of *Curcuma longa, Tribulus terrestris*, and *Dioscorea bulbifera*; hydro-methanolic extracts of *Curcuma longa, Salacia reticulata*, and *Dioscorea bulbifera*; hydro-methanolic extracts of *Curcuma longa, Tribulus terrestris*, and *Dioscorea bulbifera*; and hydro-methanolic extracts of *Curcuma longa, Tribulus terrestris, Salacia reticulata* and *Dioscorea bulbifera*.

DETAILED DESCRIPTION OF THE INVENTION

At the outset of the description, which follows, it is to be understood that the ensuing description only illustrate a particular form of the invention. However, such a particular form is only an exemplary embodiment and the teachings of the invention are not intended to be taken restrictively.

For the purpose of promoting an understanding of the principles of the invention, reference is now to be made to the embodiments illustrates and the specific language would be used to describe the same. It is nevertheless to be understood that no limitations of the scope of the invention is hereby intended, such alterations and further modifications in the illustrated bag and such further applications of the principles of the invention as illustrated therein being contemplated as would normally occur to one skilled in the art to which the invention relates.

The hydro-methanolic extract of four Ayurvedic plants *Salacia reticulata, Curcuma longa, Tribulus terrestris* and *Dioscorea bulbifera* prepared by using 50:50 ratio of water and methanol is utilized for the development of present novel formulation. In order to establish the beneficial role of test formulation a mechanism based experimental and clinical studies were carried out. The water utilized for extraction was decontaminated for any type of bacterial or abnormal growth by using reverse osmosis plant. After extraction the active molecules was identified and separated by HPLC, HPTLC and NMR procedures.

The biological property was determined on the basis of mode of action of single plant selected for preparation of formulation as well as combined formulation by validation of its role in adiponectin enhancing effects in particular and improvement in other abnormalities like insulin resistance, abnormal lipids, oxidized LDL-c and triglycerides, atherosclerotic process, inflammatory process and also reduction in leptin and resistin adipocytes in metabolic syndrome patients.

Before utilizing the drug for human consumption the pre-clinical safety and efficacy profile of single as well as combined formulation were carried out following international norms. The anti-obesity, anti-atherosclerotic and blood glucose lowering activity of test drug was evaluated in experimental models. The animal model of high fat diet induced obesity, high cholesterol diet induced atherosclerosis and streptozotocin induced hyperglycemia for diabetes was designed and beneficial role of test formulation was evaluated on adiponectin, leptin, resistin, blood glucose levels, LDL-c, triglycerides, IL-6, TNF-α and hs CRP in the above experimental models. A mechanism based study indicated the therapeutic potential of the test drug in the prevention and management of metabolic syndrome through its adiponectin enhancing activity.

Extraction Procedure:

The shed dried root of *Salacia reticulata*, rhizome of *Curcuma longa*, fruits of *Tribulus terrestris* and rhizome of *Dioscorea bulbifera* were separately utilized for obtaining extracted material of the plants. The hydro-methanol extract of the plants were utilized to determine the presence of specific active molecule/active compound in a particular extracted material. After identification and separation of active compound the molecular characterization of plant extracts was carried out by using IR and NMR.

Figure 1C:
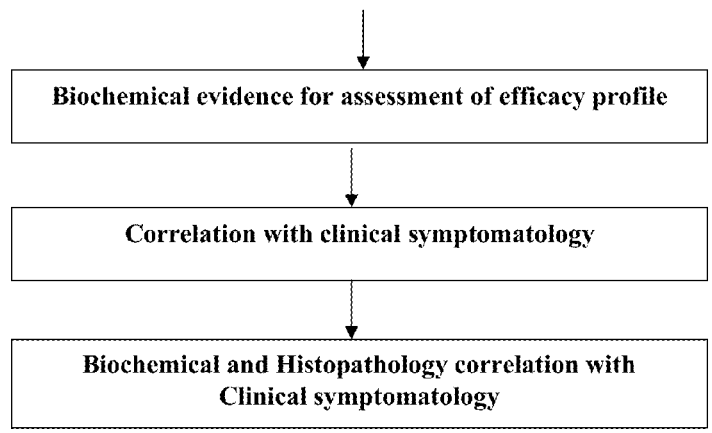
FIG. 1(c) shows. Flow Diagram of the process.

The extraction was done at the temperature of 60-70° c. and the pH of the solution was maintained at 6-8. The steps, as indicated in FIG. 1(a), FIG. 1(b) and FIG. 1 (c), were carried out to isolate the active compound, to assess the biological activity of test formulation and to develop a new drug entity. (See FIG. 1(a), FIG. 1(b) and FIG. 1 (c))

According to this invention there is provided a plant based Ayurvedic formulation showing efficacy in the prevention and management of metabolic syndrome through its adiponectin enhancing property. The present Ayurvedic test formulation comprising on the following ingredients—

1. *Salacia reticulata* (Saptachakra)—Root and fruits
2. *Tribulus terrestris* (Gokshur)—Fruits
3. *Curcuma longa* (Haridra)—Rhizome
4. *Dioscorea bulbifera* (Varahikand)—Rhizome (yam)

Preferable the aforesaid plants are present in the following doses in the test formulation—

|   | Name of the plants | Dose |
|---|---|---|
| 1. | Salacia reticulata | 250-450 mg/day |
| 2. | Tribulus terrestris | 175-375 mg/day |
| 3. | Curcuma longa | 125-250 mg/day |
| 4. | Dioscorea bulbifera | 250-425 mg/day |

The formulation may also comprise known additives such as minerals, vitamins, salts, filler (for capsulation or to prepare syrup) and binders, if required to present in trace amount.

Thus any known additive or supplement is added to prepare the final formulation as required and present in trace amount. Reference is made here in capsule form. However, it would be apparent that the preparation may also be in the form of syrup/tablet.

Preferably but without implying any limitation the present preparation comprises—

|   | Name of the plants | Dose |
|---|---|---|
| 1. | Salacia reticulata | 300 mg/day |
| 2. | Tribulus terrestris | 225 mg/day |
| 3. | Curcuma longa | 175 mg/day |
| 4. | Dioscorea bulbifera | 250 mg/day |

Hypothesis:

The present plant based Ayurvedic formulation is prepared out of the four plant extracts namely *Salacia reticulata, Tribulus terrestris, Curcuma longa* and *Dioscorea bulbifera* in effective doses. The formulation has been proven for its adiponectin enhancing property which is one of the most important biomarkers for abnormalities involved with metabolic syndrome. Thus it is proposed that abnormal lipid contents, insulin resistance, atherosclerotic process, obesity and other factors involved with metabolic syndrome cases can be managed and future risk of coronary heart disease/ischemic heart disease can be prevented by application of present test formulation.

As metabolic syndrome is a multi-factorial disorder and is a major risk factor for coronary heart disease therefore the drugs should not only be targeted to reduce body weight rather it should be equally beneficial in the management of blood pressure, insulin resistance and lipid metabolism. The present test formulation contains the extract of *Salacia reticulata* and *Dioscorea bulbifera* prominently which has shown anti-obesity, hypolipidemic, anti-atherosclerotic, anti-oxidant activity and improvement in insulin resistance in several studies.

The role of adiponectin may be considered in the development of type-2 diabetes mellitus and associated microvascular complications and can be used as an early prediction of type-2 diabetes mellitus, where as no other inflammatory and vascular marker can predict onset of diabetes. The modulation of adiponectin is helpful in the prevention and management of type-2 diabetes mellitus and its complications. A correlation has been established between low plasma adiponectin with high serum triglycerides, impaired fasting and postprandial plasma glucose concentrations. In our experimental and clinical trials the test formulation revealed that combined formulation has shown effectiveness in the treatment of obesity followed by insulin resistance and atherosclerosis. Further, several studies have shown that adiponectin exhibits anti-inflammatory properties in atherogenesis. Adiponectin also inhibits oxidized LDL induced cell proliferation and suppress cellular superoxide generation. Adiponectin alters inflammatory reactions in various pathogenesis. The cases treated with test formulation revealed lower level of blood glucose, cholesterol, triglyceride, serum insulin, leptin and increase in adiponectin compared to baseline values. Studies have indicated that dietary disogenin found in the plant *Dioscorea bulbifera* has shown lipid lowering, anti-inflammatory and blood glucose lowering effects. The mechanism of action of test drug may be that by regulating the enzymes there is increase in insulin receptor sensitivity and it inhibits these enzymes with the opposite action. The study conducted by us revealed enhanced concentration of adiponectin following test drug treatment exhibits important anti-diabetic and anti-atherogenic effects. It seems that higher adiponectin concentration may predict an increased insulin sensitivity.
About the Plants:
1. *Salacia reticulata*: This plant belongs to Celastraceae family including Hippocrataceae, also known as Saptachakra. It is climbing shrub with blackish branches. Root, bark is used for medicinal properties. It contains sitosterol, pristimerin, mangiferin, catechine, salaciquinane, triterpenoids etc. Mangiferin, salacinol and kotanelol are potent alpha-glucosidase inhibitors that have been shown to inhibit increase in serum glucose levels. Mangiferin also inhibits aldose reductase activity thereby delaying the onset or progression of diabetic complications, like diabetic neuropathy and nephropathy. Polyphenols of *salacia reticulata* catechins also contribute to the anti-diabetic property. It also has anti-obesity, anti-inflammatory role.
2. *Curcuma longa*: It belongs to Zingiberaceae family with also known as Haridra. It is found in India in abundance. The active constituent is Curcumin isolated from root of *Curcuma longa*. It has wide range of therapeutic effects. It protects against free radical damage because it is a strong anti-oxidant. It also reduces inflammation and protects the liver from number of toxic compounds. Numerous studies have shown cancer preventing effects of Curcumin and it also improves blood circulation and protect against atherosclerosis through its anti-inflammatory action.
3. *Tribulus terrestris*: belongs to zygophyllaceae family also known as Gokshur. It is found throughout India upto 11,000 ft. The active constituents is Diosgenin, gitogenin, chlorogenin, kaempferol, 3-glucoside, 3-rutinoside and tribuloside isolated from fruit and leaves of *Tribulus terrestris*. The plant *Tribulus terrestris* is one of the ingredients of present test formulation used for the treatment of arterial blood pressure and has cardiac stimulant action.
4. *Dioscorea bulbifera*: *Dioscorea bulbifera* is one of the largest plant, containing 600-800 species. It is a member of the Dioscoraceae family. Tubers of *Dioscorea* have been used throughout the world as a food and herbal medicine.

The pharmacologically active components of the *Dioscorea* species include diosgenin, which is a steroidal saponin and dioscin, a form of diosgenin with sugars attached. Recent studies suggest that dietary diosgenin may lower plasma cholesterol levels, reduce blood sugar and decrease inflammation. In numerous studies, plant steroids have been shown to lower plasma cholesterol levels. Dietary diosgenin has also shown decrease in plasma cholesterol and decrease in cholesterol absorption, liver cholesterol levels. In addition diosgenin decreased cholesterol absorption in rats, decreased plasma cholesterol and increased excretion of natural steroids.

Example-I

When the Hydro-methanolic extract of *Salacia reticulata* in the dose of 375-mg/day, *Dioscorea bulbifera* in the dose of 250 mg/day and *Tribulus terrestris* 225 mg/day mixed and given to streptozotocin induced diabetic rats increase in adiponectin concentration along with reduction in blood glucose level was noticed.

Example-II

When the hydro-methanolic extract of *Dioscorea bulbifera* in the dose of 325 mg/day, *Tribulus terrestris* in the dose of 275 mg/day and *Curcuma longa* in the dose of 175 mg/day was mixed and given to high fat diet induced obese animals decrease in triglycerides body weight blood glucose level is recorded.

Example-III

When the hydro-methanolic extract of *Dioscorea bulbifera* in the dose of 325 mg/day, *Curcuma longa* in the dose of 175 mg/day and *Salacia reticulata* in the dose of 375 mg/day mixed and orally administered to diagnosed metabolic syndrome patients increase in adiponectin concentration was estimated. Further, the inflammatory cytokines TNF-α, IL-6 along with hs-CRP also decreased after treatment. Thus the atherosclerotic process checked and improved significantly in metabolic syndrome cases.

Example-IV

When the hydro-methanolic extract of *Dioscorea bulbifera* 400 mg/day, *Tribulus terrestris* 325 mg/day and *Curcuma longa* 125 mg/day mixed and given to metabolic syndrome patients, an increase in adiponectin and decrease in leptin level resulted in reduction in total body weight and body fat indicating anti-obesity activity of test formulation.

Example-V

When the hydro-methanolic extract of *Salacia reticulata* in the dose of 425 mg/day, *Dioscorea bulbifera* in the dose of 325 mg/day and *Tribulus terrestris* in the dose of 250 mg/day mixed and given to metabolic syndrome patients reduced body mass index, abnormal lipids, blood glucose and blood pressure.

Example-VI

When the hydro-methanolic extract of *Dioscorea bulbifera* in the dose of 275 mg/day, *Salacia reticulata* in the dose of 375 mg/day, *Tribulus terrestris* in the dose of 175 mg/day and *Curcuma longa* in the dose of 125 mg/day mixed and given to metabolic syndrome patients, enhances the plasma adiponectin concentration and inhibited the pancreatic lipase enzyme with the result reduction in blood glucose level, modification in abnormal lipids including decrease of altered adipokine, leptin and inflammatory markers TNF-α, IL-6 and hs CRP was recorded.

The non-clinical and clinical safety profile assessment indicated that the drug is safe and can be given for longer time without any adverse reaction.

Experimental Pharmacology of Test Formulation
Anti-Obesity Role of Test Formulation
  Animal—female Wistar rats—6 in each group
  Weight—95-125 gm.
  Group-I: Normal control
  Group-II: Treated with Cafeteria diet
  Group-III: Treated with cafeteria diet+test formulation Cafeteria Diet:
- 1st day—condensed milk 40 gm.+bread 40 gm.
- 2nd Day—Chocolate 15 gm+biscuits 30 gm+dried coconut 30 gm.
- 3rd day—Cheese 40 gm+boiled potato 50 gm (Repeated successively up to 30 days and given to 6 rats of Group-II & III)

Parameters: Body wt., blood glucose, TC & TG, Adiponectin.

Test formulation was suspended in distilled water and administered orally in a dose of 300 mg./kg P.O. twice in a day at a constant volume of 0.5 ml/100 gm. wt. for 30 days

TABLE 1

Effect of test formulation on body wt. following cafeteria diet inexperimental rats

| Groups | Body weight (gm) | | | Comp. Initial vs after 30 days |
|---|---|---|---|---|
| | Initial | After 15 days | After 30 days | |
| Normal control (N = 6) | 104.93 ± 3.88 | 110.82 ± 6.03 | 117.36 ± 4.91 | $P < 0.001$ |
| Cafeteria diet only (N = 6) | 99.22 ± 4.37 | 128.92 ± 6.11 | 158.90 ± 12.13 | $P < 0.001$ |
| Cafeteria diet + test formulation (N = 6) | 112.38 ± 10.45 | 126.74 ± 7.90 | 137.08 ± 9.31 | $P < 0.001$ |

TABLE 2

Effect of test formulation on total cholesterol and triglycerides following cafeteria diet in experimental animals

| Groups | TC (mg/dl) | | Comp. initial vs after 30 days | Triglyceride (mg/dl) | | Comp. initial vs after 30 days |
|---|---|---|---|---|---|---|
| | Initial | After 30 days | | Initial | After 30 days | |
| Normal Control (N = 6) | 84.78 ± 4.69 | 88.36 ± 5.11 | $P > 0.05$ | 81.89 ± 8.63 | 83.01 ± 9.34 | $P > 0.05$ |
| Cafeteria diet only (N = 6) | 87.11 ± 6.94 | 91.35 ± 9.12 | $P < 0.05$ | 79.74 ± 5.80 | 98.34 ± 4.93 | $P < 0.05$ |
| Cafeteria diet + test formulation (N = 6) | 83.98 ± 7.13 | 79.45 ± 5.90 | $P < 0.05$ | 81.04 ± 5.82 | 77.83 ± 6.71 | $P < 0.05$ |

TABLE 3

Effect of test formulation on blood glucose level and adiponectin following cafeteria diet in experimental animals

| Groups | Blood glucose level (mg/dl) | | Comp. initial vs after 30 days | Adiponectin (pg/ml) | | Comp. initial vs after 30 days |
|---|---|---|---|---|---|---|
| | Initial | After 30 days | | Initial | After 30 days | |
| Normal control (N = 6) | 58.90 ± 7.02 | 55.70 ± 6.88 | $p > 0.05$ | 12.87 ± 1.91 | 13.16 ± 2.08 | $p > 0.05$ |
| Cafeteria diet only (N = 6) | 54.93 ± 6.12 | 71.11 ± 5.90 | $P < 0.001$ | — | 7.82 ± 1.03 | $P < 0.001$ |
| Cafeteria diet + test formulation (N = 6) | 57.91 ± 5.16 | 63.90 ± 4.23 | $P < 0.01$ | — | 9.37 ± 1.52 | $P < 0.01$ |

TABLE 4

Role of hydro alcoholic extract of *Dioscorea bulbifera* on TC among high cholesterol diet treated rats

| Groups | Total cholesterol level (mg/dl) | | |
|---|---|---|---|
| | Initial | after 15 day | after 1 month |
| Normal control (N = 10)* | 64.32 ± 7.89 | 63.80 ± 6.52 | 64.70 ± 8.42 |

TABLE 4-continued

| | | | |
|---|---|---|---|
| High cholesterol diet (N = 10)** | — | 895.42 ± 49.75 | 480.82 ± 40.72 |
| High cholesterol diet + *Dioscorea bulbifera* (N = 10)*** | — | 738.44 ± 90.85 | 378.50 ± 38.20 |
| High cholesterol diet + statin (2.5 mg/kg/day) (N = 10)**** | — | 691.52 ± 78.85 | 280.50 ± 16.80 |

| Comparison | | | |
|---|---|---|---|
| * vs ** | P > 0.05 | P < 0.001 | P < 0.001 |
| ** vs *** | | P < 0.001 | P < 0.001 |
| *** vs **** | | P < 0.001 | P < 0.001 |

TABLE 5

Effect of test formulation on HDL-c level among high cholesterol diet treated rats

| | HDL-c level (mg/dl) | | |
|---|---|---|---|
| Groups | Initial | after 15 day | after 1 month |
| Normal control (N = 10)* | 22.50 ± 4.33 | 23.32 ± 2.85 | 22.37 ± 3.85 |
| High cholesterol diet (N = 10)** | — | 17.82 ± 5.32 | 13.85 ± 1.85 |
| High cholesterol diet + Test formulation (N = 10)*** | — | 19.60 ± 3.85 | 21.20 ± 3.85 |
| High cholesterol diet + Statin (2.5 mg/kg/day)(N = 10)**** | — | 20.32 ± 4.85 | 21.85 ± 3.85 |

| Comparison | | | |
|---|---|---|---|
| * vs ** | P > 0.05 | P < 0.05 | P < 0.001 |
| ** vs *** | | P > 0.05 | P < 0.001 |
| *** vs **** | | P > 0.05 | P < 0.05 |

TABLE 6

Effect of test formulation on LDL-c level among high cholesterol diet treated rats

| | LDL-c level (mg/dl) | | |
|---|---|---|---|
| Groups | Initial | after 15 day | after 1 month |
| Normal control (N = 10)* | 23.85 ± 4.78 | 22.75 ± 5.72 | 24.22 ± 6.85 |
| High cholesterol diet (N = 10)** | — | 341.50 ± 62.32 | 314.40 ± 48.34 |
| High cholesterol diet + Test formulation (N = 10)*** | — | 274.50 ± 41.93 | 142.55 ± 32.08 |
| High cholesterol diet + Statin (2.5 mg/kg/day) (N = 10)**** | — | 255.80 ± 37.38 | 108.85 ± 16.85 |

| Comparison | | | |
|---|---|---|---|
| * vs ** | P > 0.05 | P < 0.001 | P < 0.001 |
| ** vs *** | | P < 0.05 | P < 0.001 |
| *** vs **** | | P > 0.05 | P < 0.05 |

TABLE 7

Effect of test formulation on Triglycerides level among high cholesterol diet treated rats

| | Triglycerides level (mg/dl) | | |
|---|---|---|---|
| Groups | Initial | after 15 day | after 1 month |
| Normal control (N = 10)* | 26.85 ± 8.70 | 30.32 ± 7.85 | 28.40 ± 5.52 |
| High cholesterol diet (N = 10)** | — | 340.70 ± 64.80 | 298.50 ± 39.32 |
| High cholesterol diet + Test formulation (N = 10)*** | — | 260.55 ± 69.85 | 174.93 ± 21.78 |
| High cholesterol diet + Statin (2.5 mg/kg/day) (N = 10)**** | — | 228.50 ± 31.80 | 112.85 ± 19.30 |

| Comparison | | | |
|---|---|---|---|
| * vs ** | P > 0.05 | P < 0.001 | P < 0.001 |
| ** vs *** | | P < 0.05 | P < 0.01 |
| *** vs **** | | P > 0.05 | P < 0.05 |

Clinical Study:

Material & Methods:

The study population consisted of 128 diagnosed Metabolic Syndrome cases (76 Men and 52 Women), aged 52.81±9.68 years at study entry. The cases were diagnosed as per criteria given by WHO for classification and diagnosis of Metabolic Syndrome.

Selection Criteria

| | |
|---|---|
| Waist circumference 100 cm | (>40″ inches chest for men) |
| | (>35″ inches chest for women) |
| Blood pressure | >130 mm Hg systolic |
| | >85 mm Hg diastolic |
| Fasting glucose | >100 mg/dl |
| Triglycerides | >150 mg/dl |
| HDL | <40 mg/dl for men and |
| | <50 mg/dl for women |

After preliminary screening the subjects showing association with 3 or more than 3 above factors were selected. The clinical trial was conducted in three groups—

Group-I: 36 cases were treated with Orlistat (120 mg twice a day after each meals).

Group-II: 44 cases were treated with Ayurvedic formulation.

Group-III: 48 cases were administered Orlistat along with Ayurvedic formulation.

Method:

Body mass index (BMI) was calculated following formula {weight (kg)÷ height ($m_2$)} and anthropometer was used for circumference measurement. Lipid profile including triglyceride was estimated by standard laboratory kits. TNF-□, interleukin-6 was measured by ELISA kit, adiponectin by radioimmunoassay kit. CRP by kit for quantitative nephelometric determination of CRP in human serum or plasma by Turbox/Turbox analyzer and ELISA activity assay kit for Leptin level. Subjects suffering from any other disease known to affect the study parameters were excluded from the series. Upon recruitment all subjects gave informed written consent.

TABLE 1

Figure 2:
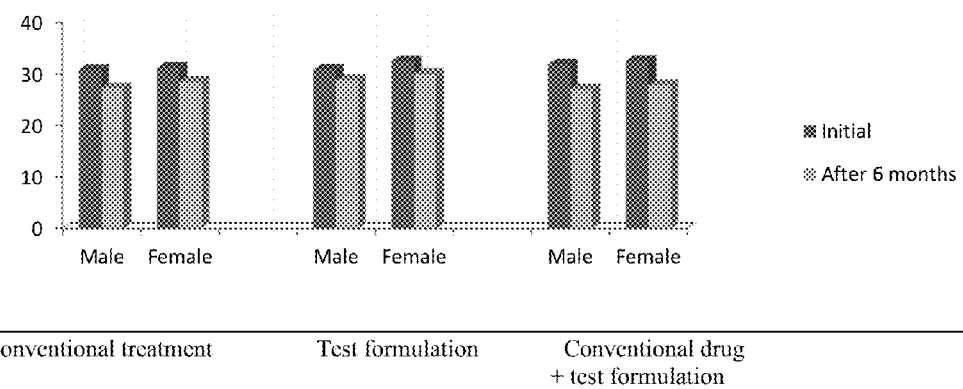
FIG. 2. Reduction in body mass Index following test drug treatment in Metabolic Syndrome Cases.

Reduction in Body Mass Index following test drug treatment in Metabolic Syndrome cases. (FIG. 2)

| Treatment groups | Sex | No. of cases | Body Mass Index (BMI) Initial | After 3 months | After 6 months | Comp. Initial vs After 6 months |
|---|---|---|---|---|---|---|
| Conventional drug treatment | Male | 21 | 30.75 ± 2.17 | 28.82 ± 1.90 | 27.16 ± 1.35 | $P < 0.001$ |
|  | Female | 15 | 31.14 ± 1.88 | 29.68 ± 2.04 | 28.45 ± 1.68 | $P < 0.001$ |
| Test formulation treatment | Male | 28 | 30.81 ± 2.13 | 29.60 ± 1.94 | 28.73 ± 1.56 | $P < 0.001$ |
|  | Female | 16 | 32.41 ± 1.75 | 30.69 ± 2.11 | 29.98 ± 1.73 | $P < 0.001$ |
| Conventional drug + test formulation treatment | Male | 27 | 31.75 ± 2.16 | 29.38 ± 2.13 | 26.93 ± 1.84 | $P < 0.001$ |
|  | Female | 21 | 32.52 ± 1.45 | 29.74 ± 1.82 | 27.82 ± 1.35 | $P < 0.001$ |
| Normal range: |  | 18-24 |  |  |  |  |

TABLE 2

Figure 3:
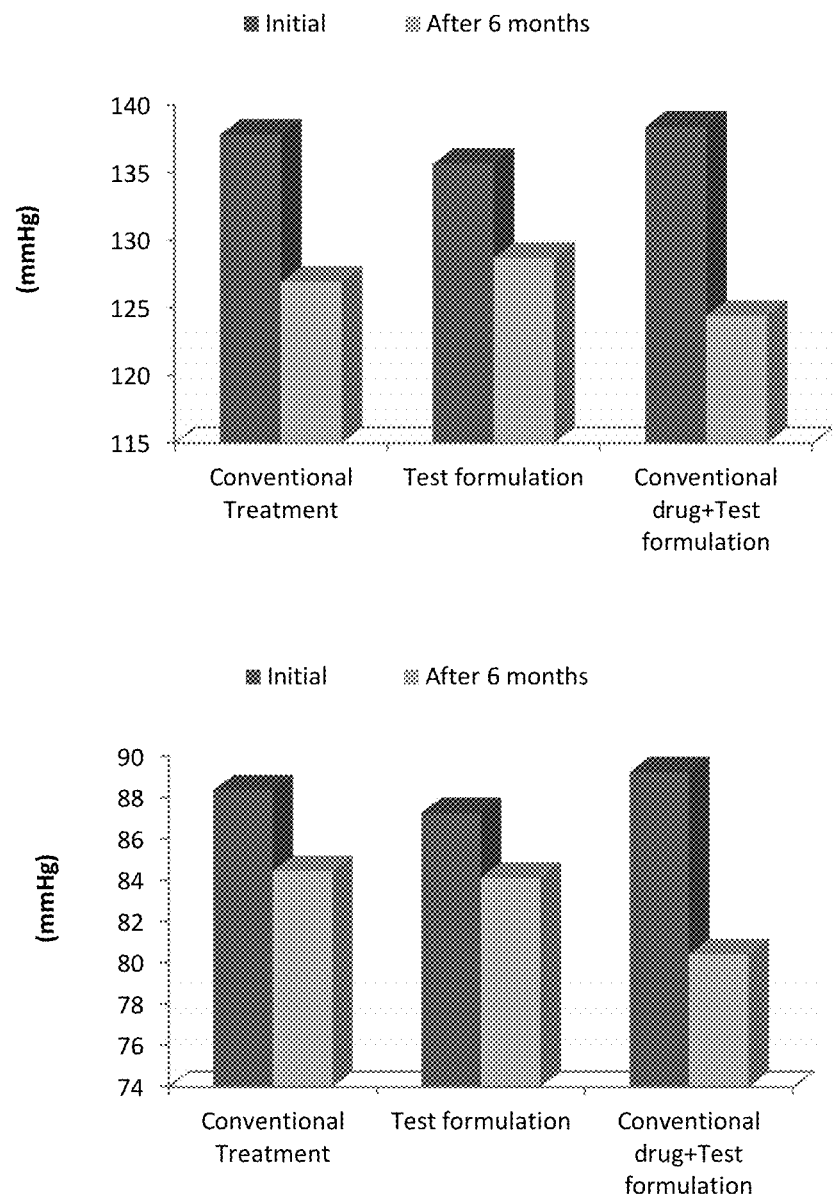
FIG. 3. Beneficial effect of test formulation on blood pressure in Metabolic Syndrome cases.

Beneficial effect of test formulation on blood pressure in Metabolic Syndrome cases (FIG. 3)

| Treatment groups | No. of cases | Systolic blood pressure (mmHg) Initial | After 6 months | Comp. Initial vs After 6 months | Diastolic blood pressure (mmHg) Initial | After 6 months | Comp. Initial vs After 6 months |
|---|---|---|---|---|---|---|---|
| Conventional drug treatment | 36 | 137.82 ± 5.15 | 126.90 ± 4.06 | $P < 0.001$ | 88.35 ± 2.06 | 84.42 ± 1.98 | $P < 0.001$ |
| Test formulation treatment | 44 | 135.65 ± 6.11 | 128.68 ± 3.97 | $P < 0.001$ | 87.27 ± 2.34 | 84.11 ± 2.01 | $P < 0.001$ |
| Conventional drug + test formulation treatment | 48 | 138.41 ± 5.87 | 124.42 ± 4.90 | $P < 0.001$ | 89.24 ± 1.88 | 80.41 ± 1.06 | $P < 0.001$ |

TABLE 3

Figure 4:
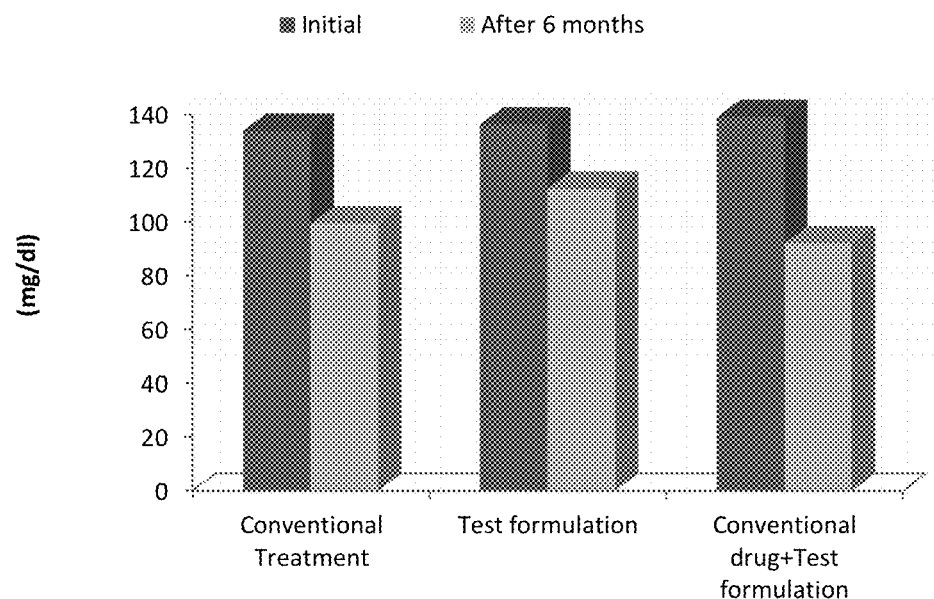
FIG. 4. Decrease in blood glucose level following test drug treatment in Metabolic Syndrome cases.
Figure 4:
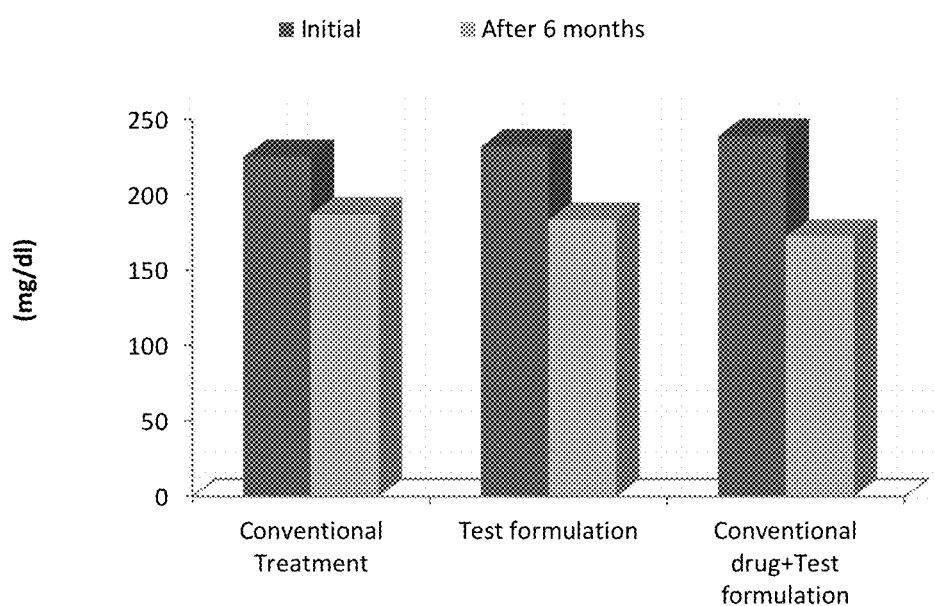

Decrease in blood glucose levels following test drug treatment in Metabolic Syndrome cases (FIG. 4)

| Treatment groups | No. of cases | Fasting blood glucose (mg/dl) Initial | After 6 months | Comp. Initial vs After 6 months | Postprandial blood glucose (mg/dl) Initial | After 6 months | Comp. Initial vs After 6 months |
|---|---|---|---|---|---|---|---|
| Conventional drug treatment | 36 | 133.90 ± 8.82 | 99.43 ± 4.36 | $P < 0.001$ | 224.81 ± 20.14 | 186.90 ± 17.42 | $P < 0.001$ |
| Test formulation treatment | 44 | 136.22 ± 7.93 | 112.41 ± 5.11 | $P < 0.001$ | 231.64 ± 23.71 | 183.42 ± 15.84 | $P < 0.001$ |
| Conventional drug + test formulation treatment | 48 | 138.97 ± 9.86 | 91.82 ± 5.74 | $P < 0.001$ | 238.70 ± 31.64 | 172.08 ± 21.3 | $P < 0.001$ |

TABLE 4

Figure 5:
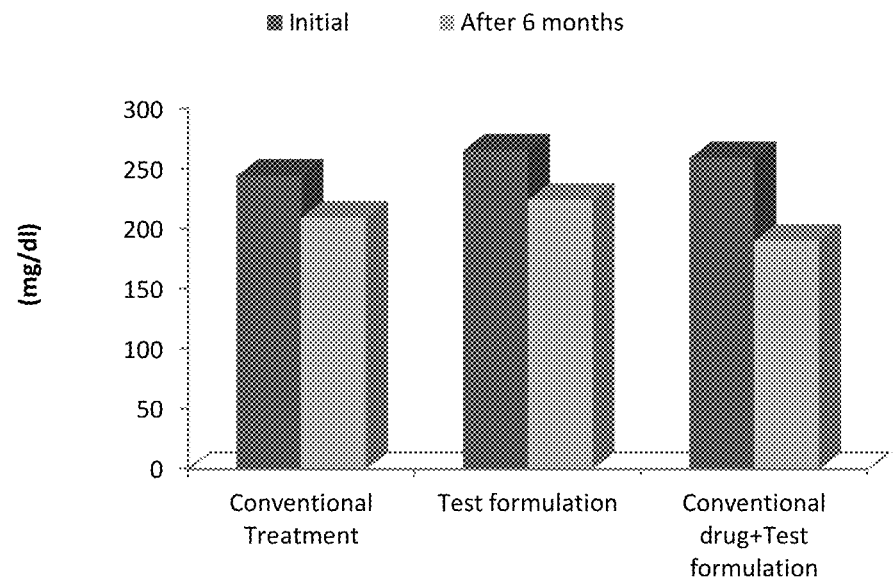
FIG. 5. Decline in total cholesterol and triglycerides concentration following test drug treatment in Metabolic Syndrome Cases.
Figure 5:
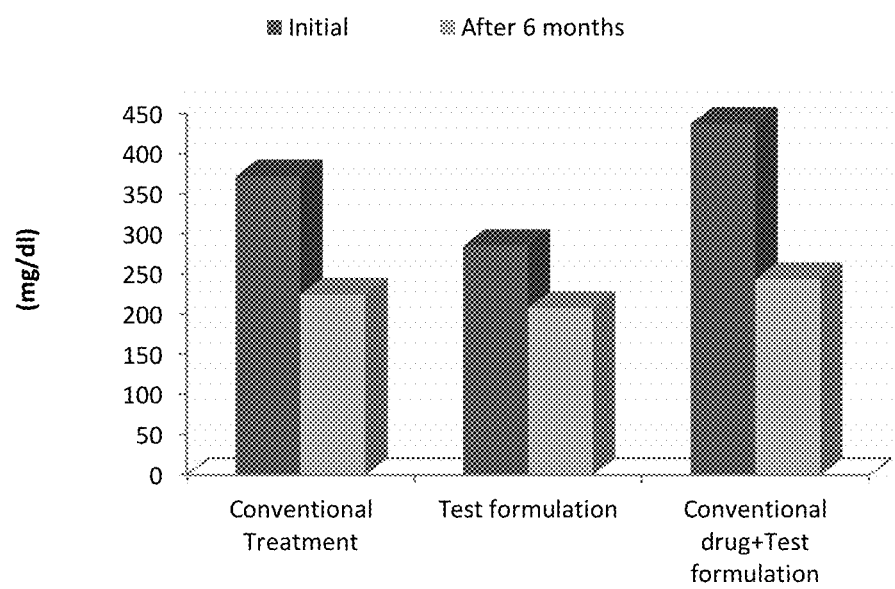

Decline in total cholesterol and triglycerides concentration following test drug treatment in Metabolic Syndrome cases. (FIG. 5)

| Treatment groups | No. of cases | Total cholesterol (mg/dl) Initial | Total cholesterol (mg/dl) After 6 months | Comp. Initial vs After 6 months | Triglycerides (mg/dl) Initial | Triglycerides (mg/dl) After 6 months | Comp. Initial vs After 6 months |
|---|---|---|---|---|---|---|---|
| Conventional drug treatment | 36 | 243.84 ± 41.52 | 208.91 ± 27.97 | P < 0.001 | 371.90 ± 43.88 | 224.56 ± 37.90 | P < 0.001 |
| Test formulation treatment | 44 | 264.9 ± 38.22 | 223.75 ± 29.45 | P < 0.001 | 284.87 ± 34.82 | 207.83 ± 24.77 | P < 0.001 |
| Conventional drug + test formulation treatment | 48 | 258.5 ± 27.90 | 189.78 ± 26.11 | P < 0.001 | 436.98 ± 51.30 | 243.80 ± 34.93 | P < 0.001 |
| Normal range: | | 150-200 (mg/dl) | | | ≤150 (mg/dl) | | |

TABLE 5

Figure 6:
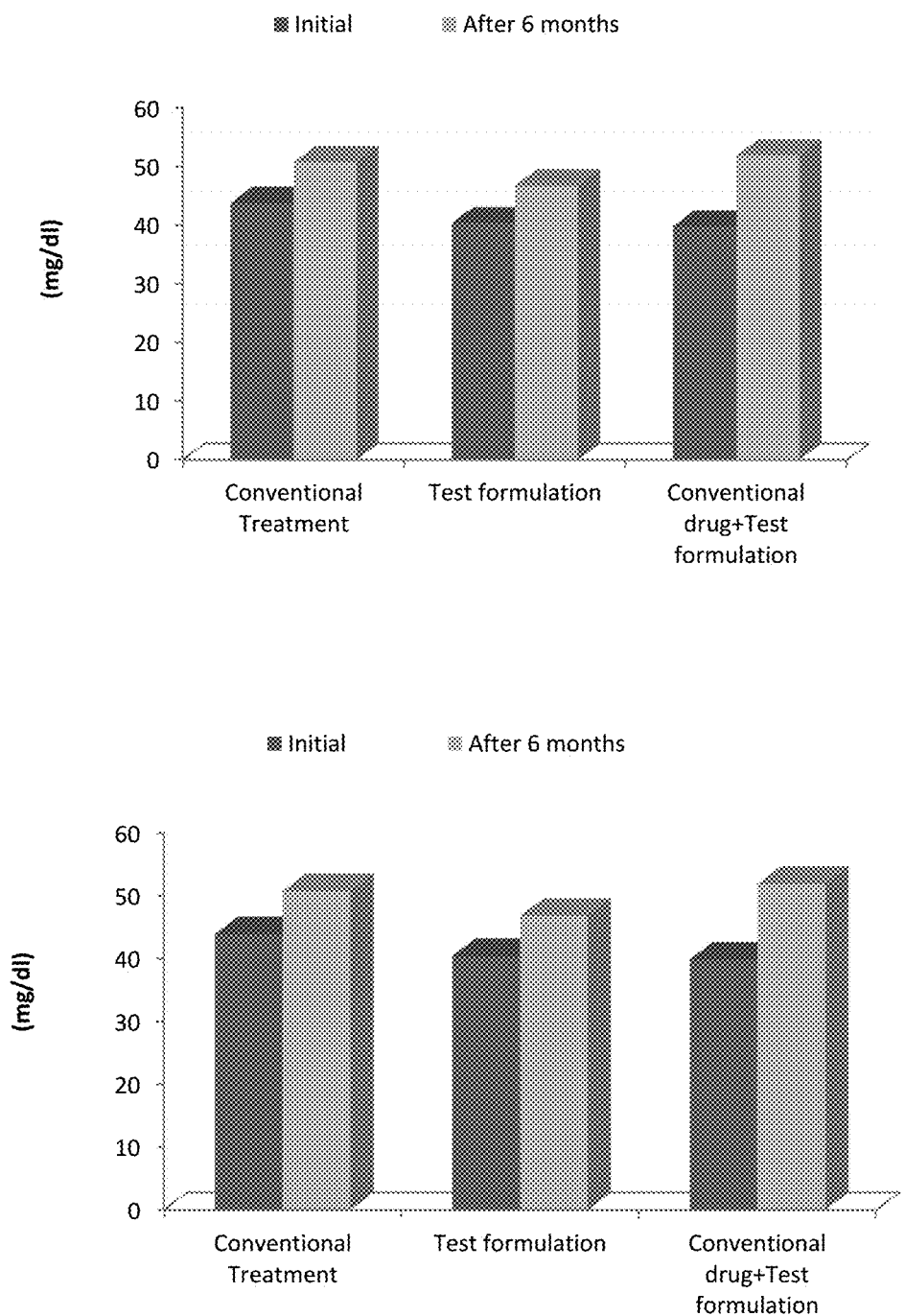
FIG. 6. Beneficial role of test drug on LDL-c and HDL-c among Metabolic Syndrome Cases.

Beneficial role of test drug on LDL-c and HDl-c among Metabolic Syndrome cases. (FIG. 6)

| Treatment groups | No. of cases | LDL-c (mg/dl) Initial | LDL-c (mg/dl) After 6 months | Comp. Initial vs After 6 months | HDL-c (mg/dl) Initial | HDL-c (mg/dl) After 6 months | Comp. Initial vs After 6 months |
|---|---|---|---|---|---|---|---|
| Conventional drug treatment | 36 | 143.71 ± 9.13 | 109.42 ± 8.44 | P < 0.001 | 43.84 ± 2.42 | 50.75 ± 3.12 | P < 0.001 |
| Test formulation treatment | 44 | 150.35 ± 8.56 | 127.91 ± 7.35 | P < 0.001 | 40.38 ± 3.17 | 46.81 ± 2.46 | P < 0.001 |
| Conventional drug + test formulation treatment | 48 | 148.43 ± 8.04 | 101.87 ± 5.94 | P < 0.001 | 39.82 ± 2.90 | 51.90 ± 2.87 | P < 0.001 |
| Normal range: | | ≤100 (mg/dl) | | | ≥45 (mg/dl) | | |

TABLE 6

Figure 7:
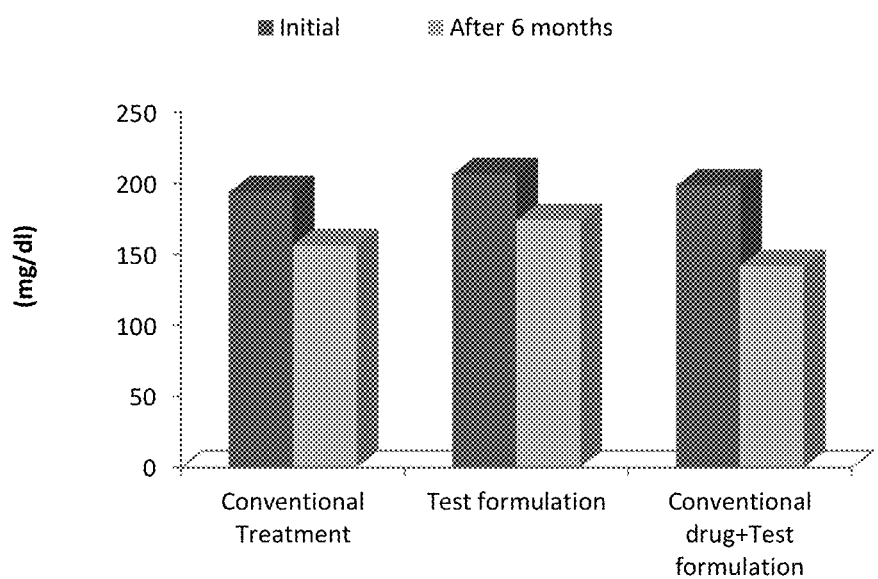
FIG. 7. Beneficial role of test drug on apolipo (B) among Metabolic Syndrome Cases.
Figure 8:
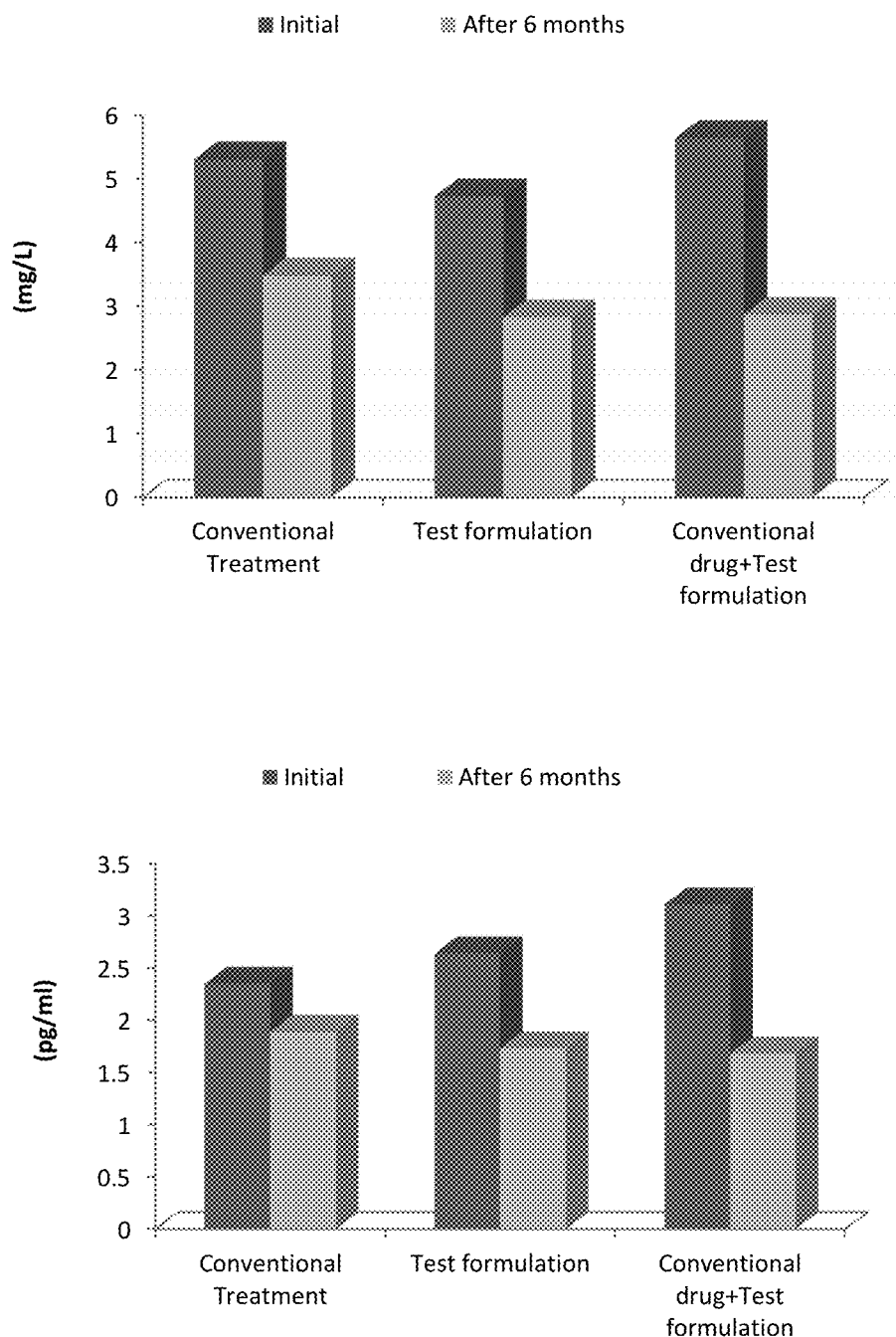
FIG. 8. Regulation of pro-inflammatory cytokines following drug treatment in Metabolic Syndrome Cases.

Beneficial role of test drug on apolipo (B) among Metabolic Syndrome cases. (FIG. 7)

| Treatment groups | No. of cases | Apolipo (B) (mg/dl) Initial | Apolipo (B) (mg/dl) After 6 months | Comp. Initial vs After 6 months |
|---|---|---|---|---|
| Conventional drug treatment | 36 | 193.88 ± 31.64 | 156.41 ± 17.11 | P < 0.001 |
| Test formulation treatment | 44 | 206.45 ± 29.81 | 173.90 ± 23.64 | P < 0.001 |
| Conventional drug + test formulation treatment | 48 | 198.43 ± 27.93 | 141.79 ± 23.14 | P < 0.001 |
| Normal range: | | 55-159 (mg/dl) | | |

TABLE 7

Regulation of pro-inflamamtory cytokines following test drug treatment in Metabolic Syndrome cases

| Treatment groups | No. of cases | hs CRP (mg/L) Initial | After 6 months | Comp. Initial vs After 6 months | Interleukin-6 (pg/ml) Initial | After 6 months | Comp. Initial vs After 6 months |
|---|---|---|---|---|---|---|---|
| Conventional drug treatment | 36 | 5.31 ± 1.04 | 3.48 ± 0.89 | P < 0.001 | 2.35 ± 0.84 | 1.89 ± 0.75 | P < 0.05 |
| Test formulation treatment | 44 | 4.73 ± 1.10 | 2.83 ± 0.85 | P < 0.001 | 2.64 ± 0.81 | 1.73 ± 0.52 | P < 0.001 |
| Conventional drug + test formulation treatment | 48 | 5.64 ± 1.21 | 2.87 ± 0.64 | P < 0.001 | 3.11 ± 0.94 | 1.68 ± 0.73 | P < 0.05 |
| Normal range: | | 1-3 (mg/L) | | | <1 (pg/ml) | | |

TABLE 8

Figure 9:
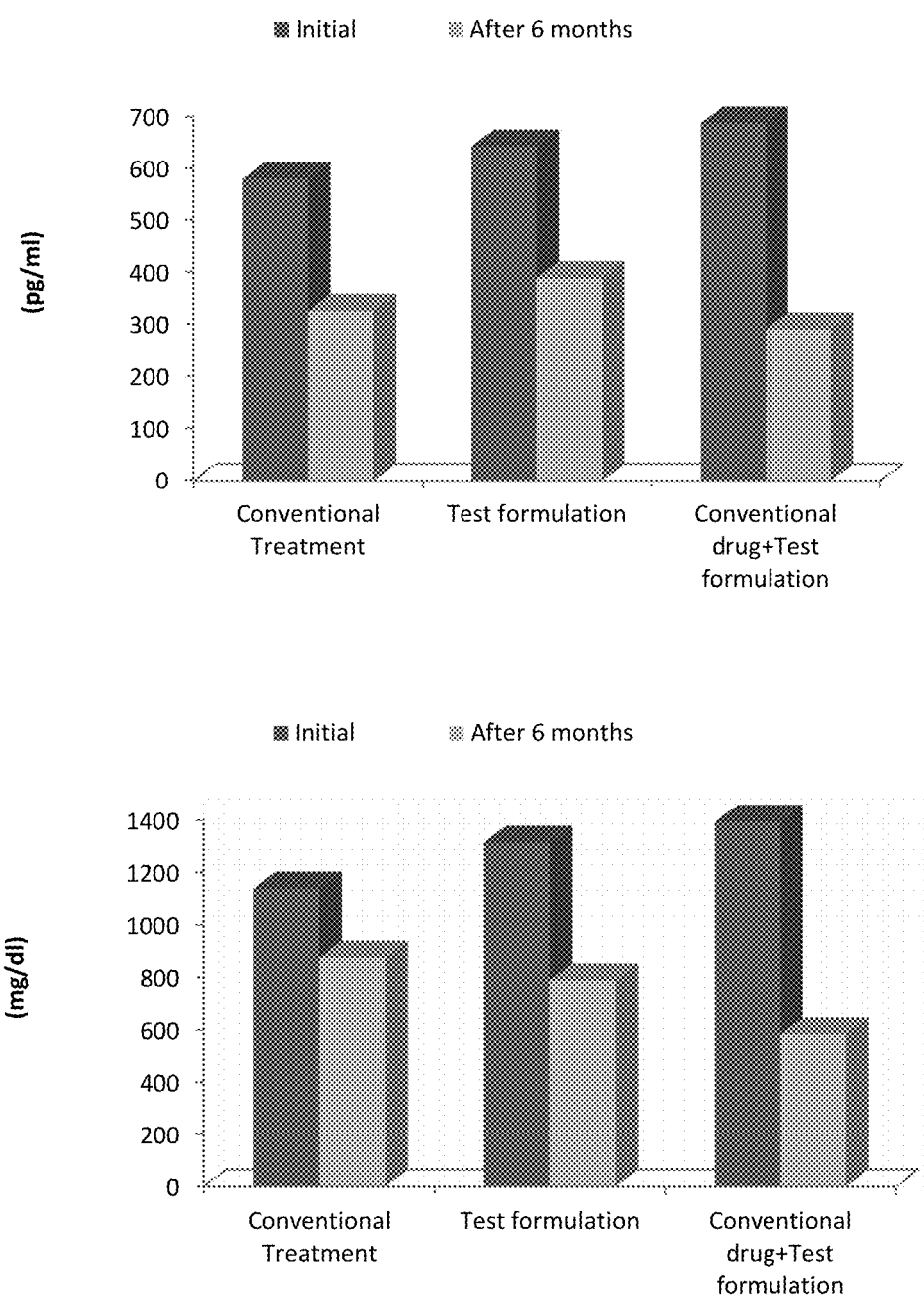
FIG. 9. Decrease in TNF-α and Endothelin concentration following test drug treatment in Metabolic Syndrome Cases.

Decrease in TNF-α and Endotheline concentration following test drug treatment in Metabolic Syndrome cases (FIG. 9)

| Treatment groups | No. of cases | TNF-α (pg/ml) Initial | After 6 months | Comp. Initial vs After 6 months | Endotheline (pg/ml) Initial | After 6 months | Comp. Initial vs After 6 months |
|---|---|---|---|---|---|---|---|
| Conventional drug treatment | 36 | 579.84 ± 68.36 | 324.85 ± 57.86 | P < 0.001 | 1139.73 ± 211.54 | 875.42 ± 171.36 | P < 0.001 |
| Test formulation treatment | 44 | 642.75 ± 64.73 | 387.90 ± 51.42 | P < 0.001 | 1314.80 ± 319.34 | 788.63 ± 153.93 | P < 0.001 |
| Conventional drug + test formulation treatment | 48 | 687.40 ± 69.91 | 289.75 ± 42.89 | P < 0.001 | 1394.36 ± 279.41 | 582.97 ± 107.25 | P < 0.001 |
| Normal range: | | 25-800 (pg/ml) | | | 0.32-1000 pg/ml | | |

TABLE 9

Figure 10:
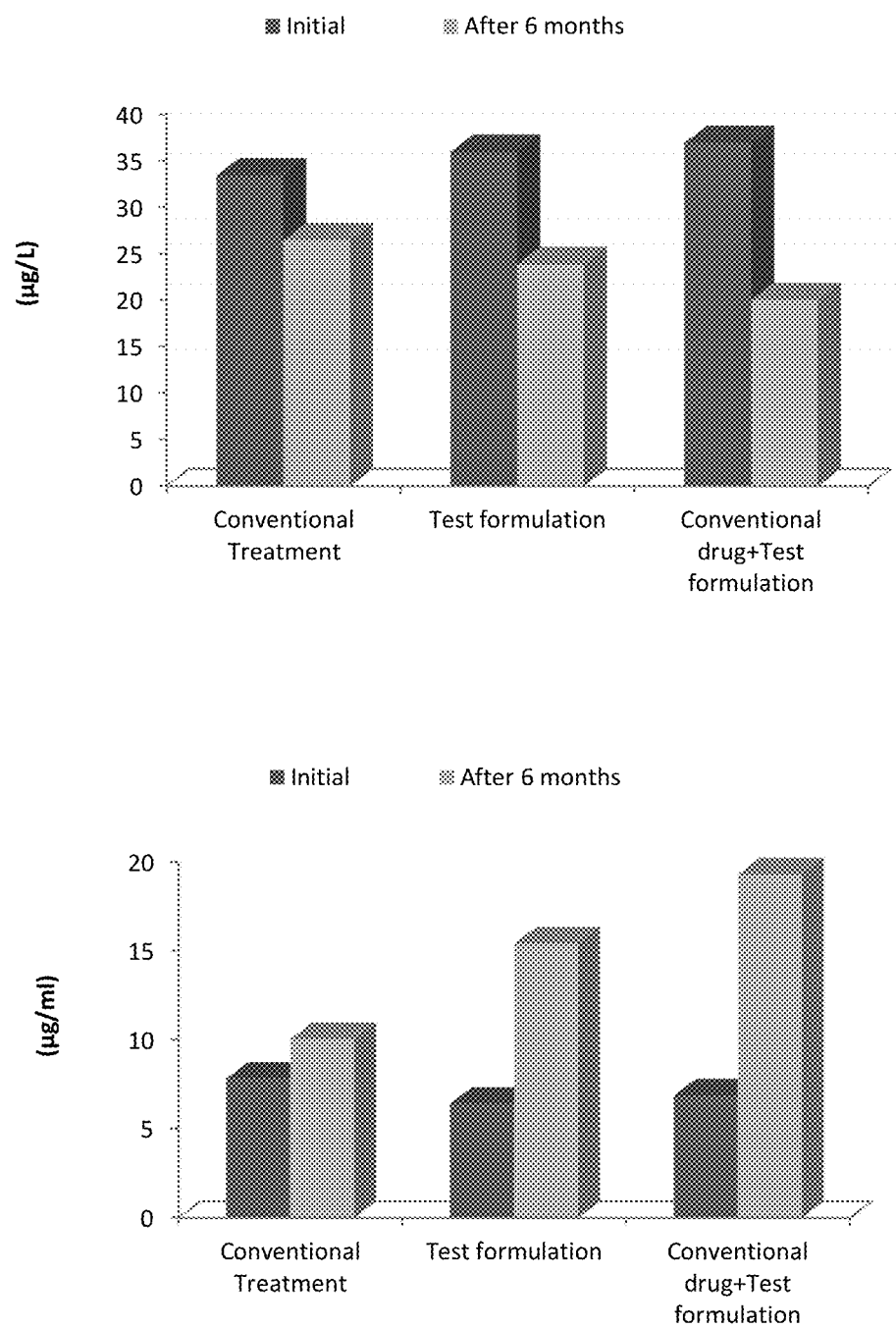
FIG. 10. Effect of test drug on Leptin and Adiponectin concentration in Metabolic Syndrome Cases.

Effect of test drug on Leptin and Adiponectin concentration in Metabolic Syndrome cases (FIG. 10)

| Treatment groups | No. of cases | Leptin (μg/L) Initial | After 6 months | Comp. Initial vs After 6 months | Adiponectin (μg/ml) Initial | After 6 months | Comp. Initial vs After 6 months |
|---|---|---|---|---|---|---|---|
| Conventional drug treatment | 36 | 33.41 ± 4.35 | 26.44 ± 3.28 | P < 0.001 | 7.82 ± 1.64 | 10.04 ± 2.84 | P < 0.001 |
| Test formulation treatment | 44 | 35.94 ± 6.11 | 23.87 ± 2.98 | P < 0.001 | 6.41 ± 0.97 | 15.42 ± 2.12 | P < 0.001 |
| Conventional drug + test formulation treatment | 48 | 36.90 ± 6.34 | 20.04 ± 3.87 | P < 0.001 | 6.87 ± 1.04 | 19.31 ± 2.97 | P < 0.001 |
| Normal range: | | 5-12 (μg/L) | | | 5-30 (μg/mL) | | |

It is to be further noted that present invention is susceptible to modifications adoptions and changes by those skilled in the art. Such variant embodiments employing the concepts and features of this invention are intended to be within the scope of the present invention which is further set forth under the claims:

The invention claimed is:

1. A plant based formulation for the prevention and management of metabolic syndrome by its adiponectin enhancing property comprising an effective amount of hydro-methanolic extracts of *Salacia reticulata* root and fruits, *Tribulus terrestris* fruits, *Curcuma longa* rhizome and *Dioscorea bulbifera* rhizome and optionally additives in trace amounts;

wherein the plant based formulation is in a pharmaceutical capsule or tablet.

2. The plant based formulation as claimed in claim 1 wherein the said hydro-methanolic extract is obtained from water:methanol in the ratio of 50:50.

3. The plant based formulation as claimed in claim 1 wherein the additives are selected from minerals, vitamins, salts and binders.

4. The plant based formulation as claimed in claim 1 wherein the plant extracts are present in following effective amounts:

|   | Name of the plants | Amount |
|---|---|---|
| 1. | Salacia reticulata | 250-450 mg |
| 2. | Tribulus terrestris | 175-375 mg |
| 3. | Curcuma longa | 125-250 mg |
| 4. | Dioscorea bulbifera | 250-425 mg. |

5. A plant based formulation for management of metabolic syndrome, consisting essentially of:
   an effective amount of hydro-methanolic of extract Dioscorea bulbifera rhizome; and
   at least two hydro-methanolic extracts selected from the group consisting of Salacia reticulata root and fruit, Tribulus terrestris fruit, and Curcuma longa rhizome;
   wherein the plant based formulation is in a pharmaceutical capsule or tablet.

6. The formulation of claim 5, wherein said hydro-methanolic extract is obtained from water:methanol having a ratio of 50:50.

7. The formulation of claim 5, further comprising an additive selected from the group consisting of vitamins, minerals, salts, and binders.

8. The formulation of claim 5, wherein the plant extracts are present in an amount to provide doses of:

|   | Name of the plants | Amount |
|---|---|---|
| 1. | Salacia reticulata | 250-450 mg/day |
| 2. | Tribulus terrestris | 175-375 mg/day |
| 3. | Curcuma longa | 125-250 mg/day |
| 4. | Dioscorea bulbifera | 250-425 mg/day. |

9. A capsule or tablet for the management of metabolic syndrome comprising a plant based formulation that consists essentially of therapeutically effective amounts of hydro-methanolic extracts of Curcuma longa rhizome, Tribulus terrestris fruit, Salacia reticulata root and fruit and Dioscorea bulbifera rhizome.

* * * * *